United States Patent
Gittelson et al.

(12) 
(10) Patent No.: US 6,431,867 B1
(45) Date of Patent: Aug. 13, 2002

(54) DENTAL IMPLANT SYSTEM

(75) Inventors: Glenn Gittelson, 2 Lincoln Ave., Suite 301, Rockville Centre, NY (US) 11570; Thomas G. Ford, Orlando, FL (US)

(73) Assignee: Glenn Gittelson, Rockville Centre, NY (US)

(*) Notice: Subject to any disclaimer, the term of this patent is extended or adjusted under 35 U.S.C. 154(b) by 65 days.

(21) Appl. No.: 09/636,166

(22) Filed: Aug. 10, 2000

Related U.S. Application Data

(60) Provisional application No. 60/198,025, filed on Apr. 18, 2000.

(51) Int. Cl.$^7$ ................................................ A61C 8/00
(52) U.S. Cl. ...................................................... 433/173
(58) Field of Search ............................... 433/172, 173, 433/174, 175, 176

(56) References Cited

U.S. PATENT DOCUMENTS

| | | |
|---|---|---|
| 3,905,109 A | 9/1975 | Cohen et al. |
| 4,468,200 A | 8/1984 | Münch |
| 5,009,596 A | 4/1991 | Soderberg |
| 5,376,004 A | 12/1994 | Mena |
| 5,399,090 A | 3/1995 | Padros-Fradera |
| 5,417,568 A | 5/1995 | Giglio |
| 5,499,918 A | 3/1996 | Morgan et al. |
| 5,651,675 A | 7/1997 | Singer et al. |
| 5,674,069 A | 10/1997 | Osorio |
| 5,688,123 A | 11/1997 | Meiers et al. |
| 5,749,731 A | 5/1998 | Morgan et al. |
| 5,779,481 A | 7/1998 | Aires |
| 5,810,592 A | 9/1998 | Daftary |
| 5,813,858 A | 9/1998 | Singer |
| 5,863,200 A | 1/1999 | Hamada et al. |
| 5,871,358 A | 2/1999 | Ingber et al. |

(List continued on next page.)

FOREIGN PATENT DOCUMENTS

| | | |
|---|---|---|
| DE | 3917690 A1 | 12/1990 |
| DE | 4028855 A1 | 3/1992 |
| DE | 19509762 A1 | 9/1996 |
| FR | 2720624 | 12/1995 |
| WO | 9521589 | 2/1995 |

OTHER PUBLICATIONS

"Regeneration of the Interdental soft tissues following denudation procedures" *Journal of Clinical Periodontology*, 1982: 9: 445–459.

(List continued on next page.)

*Primary Examiner*—Nicholas D. Lucchesi
(74) *Attorney, Agent, or Firm*—Gottlieb, Rackman & Reisman, P.C.

(57) ABSTRACT

An improved dental implant system which simulates the natural root of a tooth is provided. The system includes an implant body having a facial surface aspect, lingual surface aspect and interproximal surface aspect, and which is defined by an apical portion and a coronal portion. The system also includes an implant abutment having an internal surface aspect for selective mating engagement with the coronal portion of the implant body and also having an external surface aspect. The system further includes a crown having an internal surface aspect for selective mating engagement with the external aspect of the implant abutment. Significantly, the implant body has a bone integrating external surface which, in a coronal direction, extends more along the interproximal aspect than along the facial aspect. In particular, the bone integrating external surface defines a non-bone integrating beveled surface along the facial aspect of the coronal portion of the implant body. This beveled surface does not integrate to the bone and is designed for maintaining a bony scallop and subsequent gingival scallop with papilla around the implant and for selective mating engagement or attachment with the internal aspect of the abutment during assembly of the inventive system.

14 Claims, 10 Drawing Sheets

U.S. PATENT DOCUMENTS

| | | | |
|---|---|---|---|
| 5,899,697 | A | 5/1999 | Lazzara et al. |
| 5,904,483 | A | 5/1999 | Wade |
| 6,164,969 | A | 12/2000 | Dinkelacker |
| 6,168,436 | B1 | 1/2001 | O'Brien |
| 6,174,167 | B1 | 1/2001 | Wöhrle |
| 6,283,754 | B1 | 9/2001 | Wöhrle |

OTHER PUBLICATIONS

"The Effect of the Distance From the Contact Point to the Crest of Bone on the Presence or Absence of the Interproximal Dental Papilla" *J Periodontal*, 1992; 63:995–996.

"Gingival–Colored Porcelain for Implant–Supported Prostheses in the Aesthetic Zone" *Practical Periodontics & Aesthetic Dentistry* 1998; 10(9); 1231–1240.

"Aesthetic Soft Tissue Integration and Optimized Emergence Profile: Provisionalization and Customized Impression Coping" *Practical Periodontics & Aesthetic Dentistry* 1999; 11(3); 305–314.

"Anterior Implant–Supported Reconstructions: A Surgical Challenge" *Practical Periodontics & Aesthetic Dentistry* 1999; 11(5); 551–558.

"The Effect of Inter–Implant Distance on the Height of Inter–Implant Bone Crest" *J Periodontol* 2000; 71:546–549.

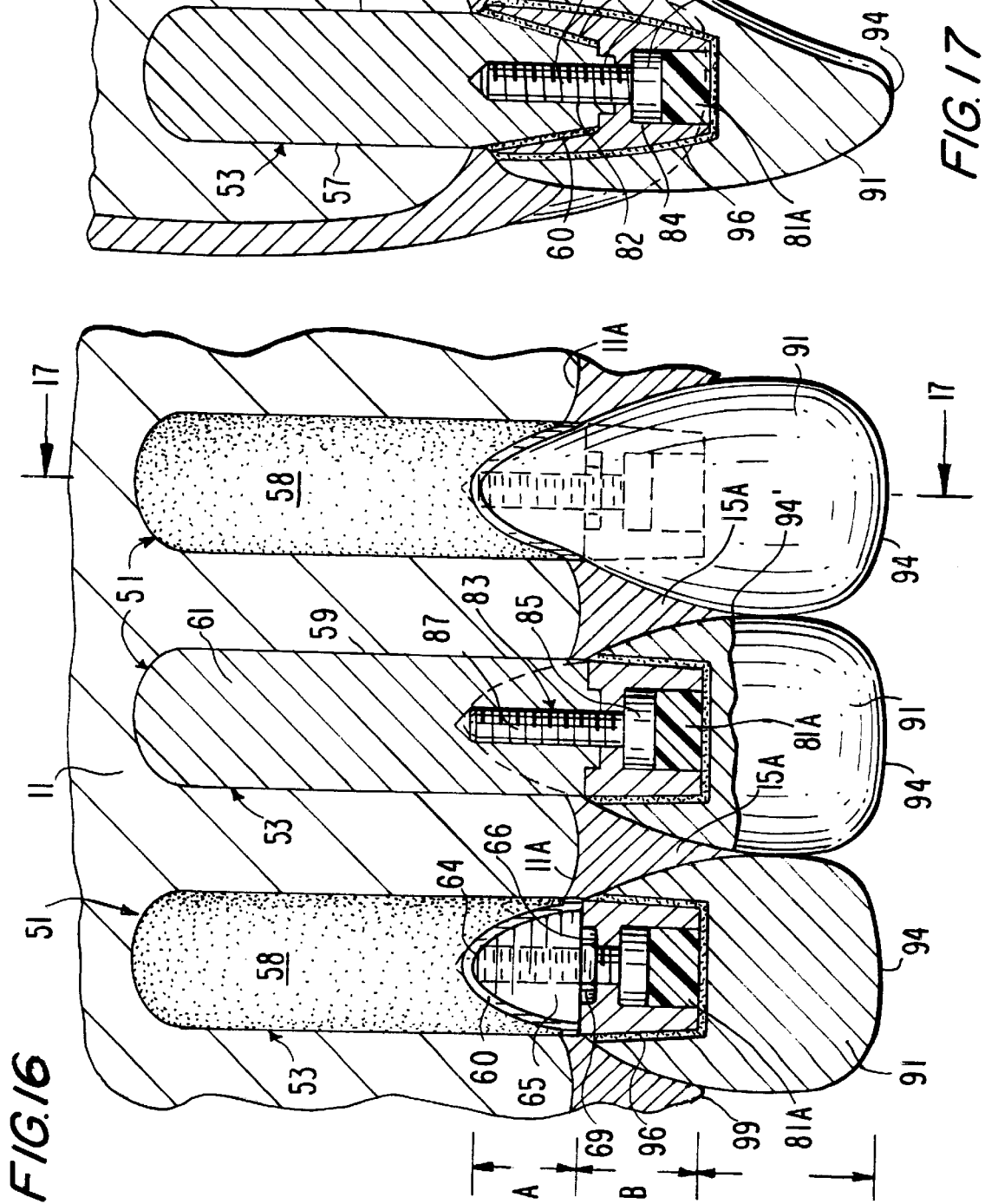

DENTAL IMPLANT SYSTEM

This application claims benefit of provisional application No. 60/198,025, filed Apr. 18,2000

BACKGROUND OF THE INVENTION

This application relates to single or multiple fixed prosthodontic restorations, and more particularly to a dental implant system which simulates the look and function of a natural root of a tooth with regard to its maintenance of bone and gingival architecture.

In the healthy non-diseased mouth with natural teeth present, there exists a biologic relationship between the root of a tooth, the crown of a tooth, the bone surrounding the root and the gingiva (soft tissue) surrounding the bone, root and crown of a tooth. In nature, the shape that the gingiva or soft tissue assumes and follows is dictated by the underlying presence and shape of bone. The contours of bone around a natural tooth is actually scalloped with the bone more apical on the facial and lingual aspects of the tooth and more coronal in the interproximal area (between the teeth). It is this scalloping of the bony architecture which lends itself to the formation and maintenance of interdental papilla (the small triangular flesh portion adjacent the gum line and located between the teeth). If the distance from the base of the papilla or tooth contact point is 5 mm or less to the interproximal bone, gingival papilla is formed and maintained in a predictable manner.

Dental implant procedures have proven to be an effective method of restoring function in patients having missing teeth. Implants provide a structure upon which a prosthetic tooth or teeth can be attached and secured in an otherwise edentulous (non-tooth) area. In contrast to using dentures or other fixed or removable dental bridge systems, implants have the advantage of maintaining bone and not being subject to decay.

A primary concern in implant dentistry is the presence of sufficient bone support, which not only is necessary for proper placement and securement of the implant itself, but is critical for the proper development and maintenance of gingival tissue including papilla that is necessary in order to achieve a desirable soft-tissue aesthetic result. Bone growth around an implant follows the shape of the bone-integrating part of the implant. With conventional side-by-side flat-ended implants, bone support between the implants is flat and therefore the gingiva between the implants is also flat. Such a flat gingival configuration produces an artificial looking, unnatural and aesthetically displeasing appearance in the patient's mouth.

Importantly, the absence of papilla between side-by-side implants used for replacing a patient's front teeth (upper or lower) may result in the formation of unaesthetic black triangles or spaces. One solution to this problem has been the use of overly contoured crown restorations. However, such crown restorations may distort natural proportional contours, leading to an unnatural, unaesthetic and unhealthy prosthesis where such is needed the most.

Grafting techniques for replacing papilla around implants have also been used, but they are almost always very costly and ineffective, especially in the case of multiple side-by-side implants. Also, grafting is less than desirable due to the typical requirement of undertaking several painful surgical procedures and the lack of predictability for success in these operations, the latter due to an inadequate amount of bone support between the implants.

Another option for overcoming the absence of papilla is the use of gingival colored porcelain (on the crowns) to cover or mask the black spaces. However, the use of gingival colored porcelain is completely unsatisfactory since the look is artificial, out of proportion, and out of contour.

Accordingly, it is desirable to provide an improved dental implant system which maintains the boney/osseo and gingival soft tissue architecture in a scalloped appearance similar to what appears around a healthy natural root of a tooth. This promotes the growth and maintenance of proper gingival tissue contours, specifically papilla, in the necessary locations along the gingival architecture such as would appear around a natural tooth.

SUMMARY OF THE INVENTION

Generally speaking, in accordance with the invention, an improved dental implant system which simulates the natural root of a tooth is provided. The system includes an implant body having a facial surface aspect, lingual surface aspect and interproximal surface aspect, and which is defined by an apical portion and a coronal portion. The system also includes an implant abutment having an internal surface aspect for selective mating engagement with the coronal portion of the implant body and also having an external surface aspect. The system further includes a crown having an internal surface aspect for selective mating engagement with the external aspect of the implant abutment.

Significantly, the implant body has a bone integrating external surface which, in a coronal direction, extends more along the interproximal aspect than along the facial aspect. In particular, the bone integrating external surface defines a non-bone integrating beveled surface along the facial aspect of the coronal portion of the implant body. This beveled surface is not integrated to the bone and is designed for maintaining a boney scallop around the implant and for selective mating engagement or attachment with the internal aspect of the implant abutment during assembly of the inventive system.

Preferably, the bone integrating external surface also defines a second non-bone integrating beveled surface along the lingual aspect of the coronal portion of the implant body. As with the first beveled surface, the second beveled surface is also designed for engagement or attachment with the internal aspect of the implant abutment.

In accordance with the invention, each beveled surface formed along the coronal portion of the implant body comprises a facial scallop having an apical extent and a coronal extent. Each beveled surface defines a taper viewed along the interproximal aspect and which extends inwardly from the apical extent to the coronal extent at an angle of an amount between about 50° and 25°.

Because the implant body of the inventive dental implant system has a bone integrating external surface which, in a coronal direction, extends more along the interproximal aspect than along the facial and lingual aspect, bone formation is naturally guided to a more apical location along the facial and lingual aspects, thereby creating a scalloped boney design around the implant body. As a result, gingival tissue is formed along the scalloped bone, promoting the formation of papilla between adjacent implants when the final prosthesis is in place with a properly located tooth contact point.

Accordingly, it is an object of the invention to provide an improved dental implant system.

Another object of the invention is to provide a dental implant system which simulates the design and function of a natural root of a tooth.

A further object of the invention is to provide a dental implant system which enables bone to be formed and maintained around the implant body thereof at two different heights or levels.

Still another object of the invention is to provide an improved dental implant system which enables the formation and maintenance of papilla between side-by-side implants and/or adjacent natural teeth.

Yet a further object of the invention is to provide a dental implant system which has a non-bone integrating beveled surface along at least a facial aspect of the coronal portion of the implant body.

Still other objects and advantages of the invention will in part be obvious and will in part be apparent from the following description.

The invention accordingly comprises the feature of construction, combination of elements and arrangement of parts as hereinafter described, and the scope of the invention will be indicated in the claims.

BRIEF DESCRIPTION OF THE DRAWINGS

For a fuller understanding of the invention, reference is made to the following description, taken in connection with the accompanying drawings, in which:

FIG. 16 is an enlarged front elevational or facial view in partial cross-section similar to what is shown in FIG. 15; and FIG. 17 is a cross-sectional view taken along line 17—17 of FIG. 16.

DETAILED DESCRIPTION OF THE PREFERRED EMBODIMENT

Figure 1:
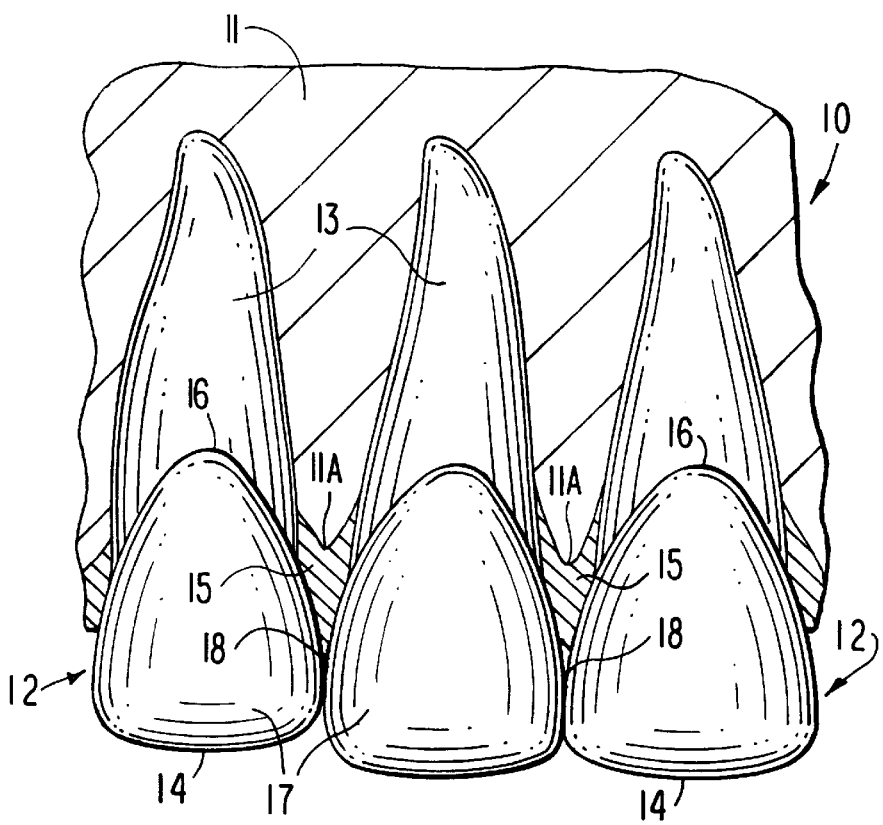
FIG. 1 is a front elevational or facial view of three side-by-side natural teeth and their corresponding roots in bone with proper tooth contacts and papilla formation.

Referring first to FIG. 1, the upper part of the mouth generally indicated at 10 and depicting a series of natural teeth is shown. Upper part of mouth 10 includes bone 11 in which three natural teeth 12 are retained. Each tooth 12 has a depending tooth crown 17 and a tooth root 13 for connection to bone 11. Each of tooth crowns 17 has an incisal edge 14 and an apical extent 16 along the crest of bone 11. As can be appreciated, bone 11, root 13 and crown 17 together define a gingival architecture having a scalloped appearance such that papilla 15 is located between teeth crowns 17 and has a base 18 which, in a coronal direction, depends more interproximally than it does along the facial area of teeth crowns 17. Base 18 is located not more than 5 mm from interproximal crestal bone 11A.

Figure 2:
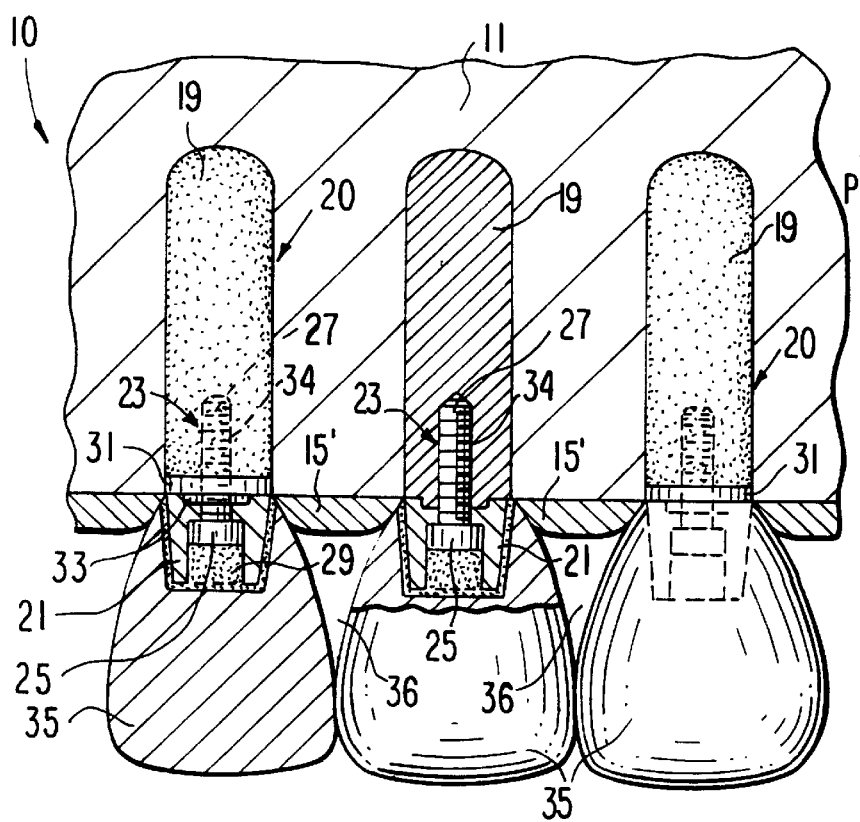
FIG. 2 is a front elevational or facial view in partial cross-section of a prior art implant design disposed in the mouth.

FIG. 2 shows a series of side-by-side prior art implant units 20 disposed in the mouth. Each implant unit 20 includes an implant body 19, an implant abutment 21 and a crown 35. Implant abutment 21 is coupled to implant body 19 by means of an abutment screw 23. Abutment screw 23 includes a screw head 25 and a threaded screw body 27. Implant body 19 is formed with a coronal plate 31 on which a threaded hex nut 33 is mounted and which overlies a screw hole 34. Implant abutment 21 is formed with a screw passage 29 which receives head 25 of abutment screw 23 when screw body 27 is engaged within screw hole 34 of implant body 19.

As can be appreciated when viewing FIG. 2, since each of implant bodies 19 is flat where it exits bone 11 (the crestal bone-implant interface), bone 11 is also flat, and thus gingival architecture is flat. As a result, papilla 15' located between implant units 20 is substantially flat in appearance, thereby creating open or black spaces 36, which are aesthetically unacceptable.

Figure 3:
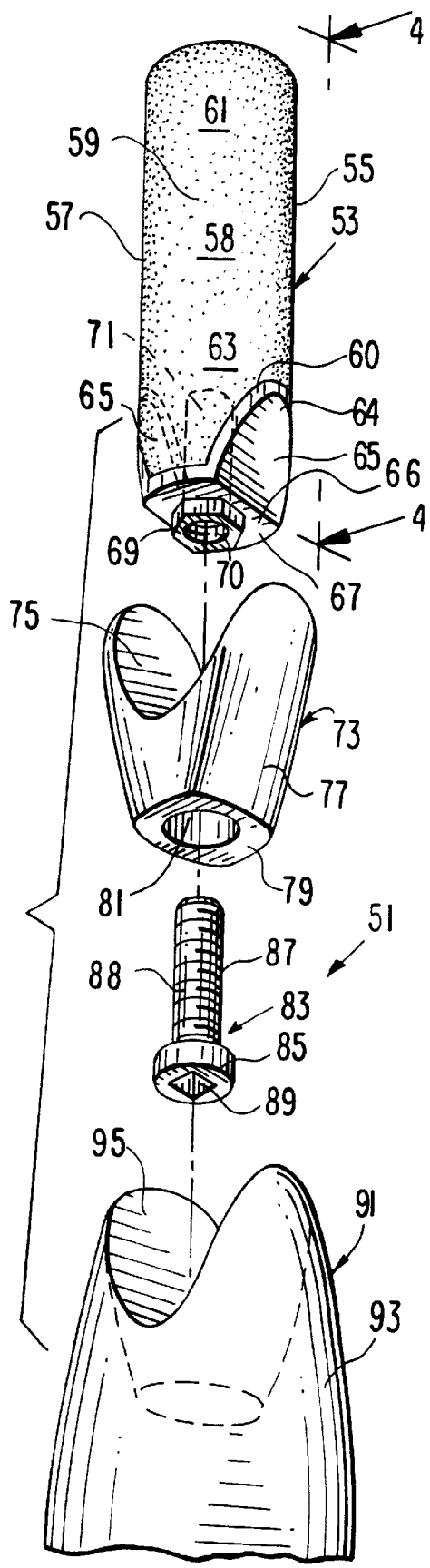
FIG. 3 is an exploded perspective view of the inventive implant system and showing the implant body, implant abutment, abutment retaining screw and crown components.
Figure 4:
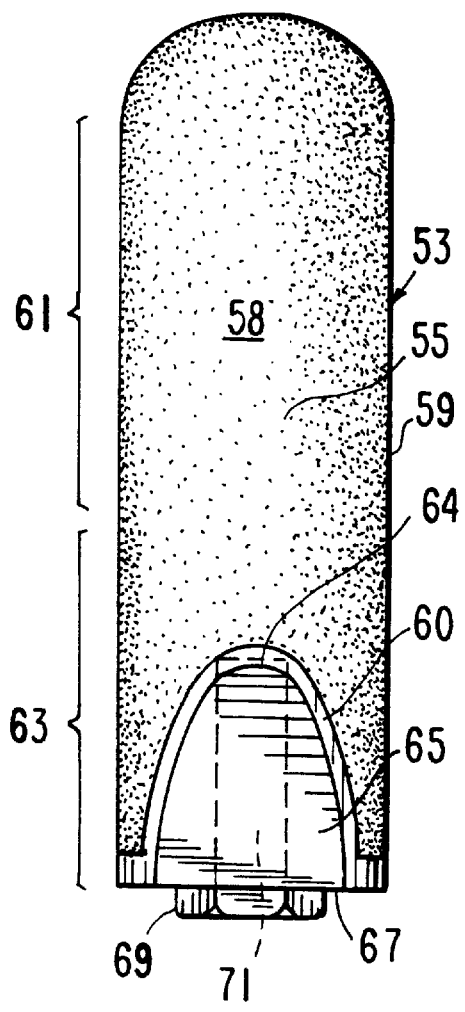
FIG. 4 is a cross-sectional view taken along line 4—4 of FIG. 3.
Figure 5:
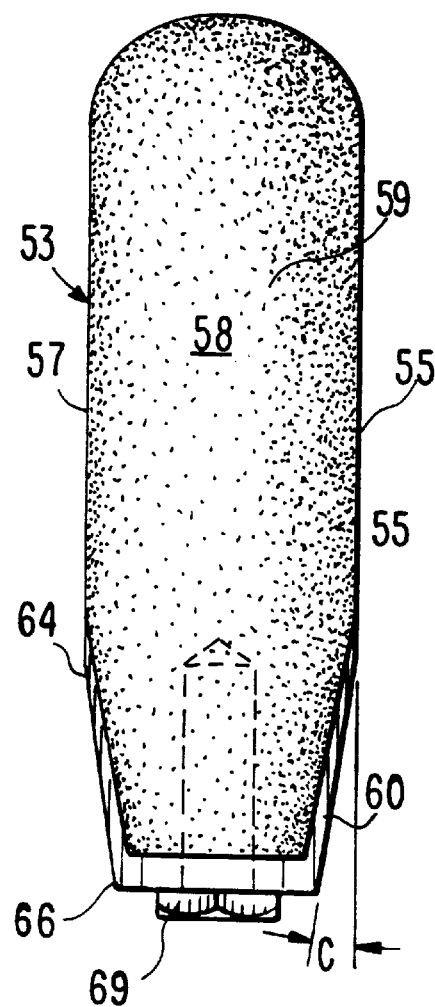
FIG. 5 is a side elevational or interproximal view of the implant body of the inventive implant system.
Figure 6:
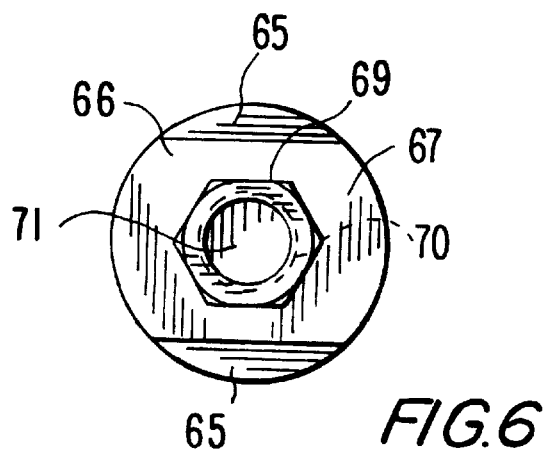
FIG. 6 is a bottom plan or coronal view of the implant body of the inventive implant system.

Referring now to FIG. 3, as well as to FIGS. 4–6, a dental implant system or assembly made in accordance with the invention is generally indicated at 51. Dental implant assembly 51 includes an implant body 53, an implant abutment 73 and a crown 91. Implant body 53 is made from a bone integrating metal material such as a titanium alloy with a roughened surface and has an elongated cylindrical configuration. Implant body 53 has a facial surface aspect 55, a lingual surface aspect 57 and an interproximal surface aspect 59. Implant body 53 consists of an apical portion 61 and a coronal portion 63. Implant body 53 has a bone integrating external surface 58 which in a coronal direction extends more along interproximal aspect 59 than along facial aspect 55 or lingual aspect 57. Bone integrating external surface 58 defines a non-bone integrating beveled surface 65 made of a machined smooth or polished metal surface along both facial aspect 55 and lingual aspect 57 of coronal portion 63 (see FIGS. 3 and 4). Each beveled surface 65 has a scalloped shape defined by an apical extent 64 and a coronal extent 66 that measures a distance A therebetween of 2 and 6 millimeters (see FIG. 16). In assembly, beveled surfaces 65 are designed for maintaining a boney scallop around coronal portion 63 of implant body 53 and for mating engagement with implant abutment 73, as discussed below.

Implant body 53 also includes a coronal plate 67 of polished or machined smooth metal on which a hex nut 69 is mounted (see FIG. 6). Hex nut 69 has a series of internal threads 70 and leads into a screw hole 71 which also has internal threads formed inside coronal portion 63 of implant body 53 for selectively receiving the body of a retaining abutment screw, as described later on.

Between bone integrating external surface 58 and non bone-integrating beveled surfaces 65, there is formed a smooth, thin non-bone integrating collar 60 which follows the scalloped shape of beveled surfaces 65 and also runs interproximally adjacent coronal plate 67. Collar 60 is also polished or machine smooth metal and has a width of between about ½ mm to 1 mm. Collar 60 serves as an interface for the gingival architecture to adhere thereto and thereby initiate the scalloped appearance of the gingival tissue.

Figure 13:
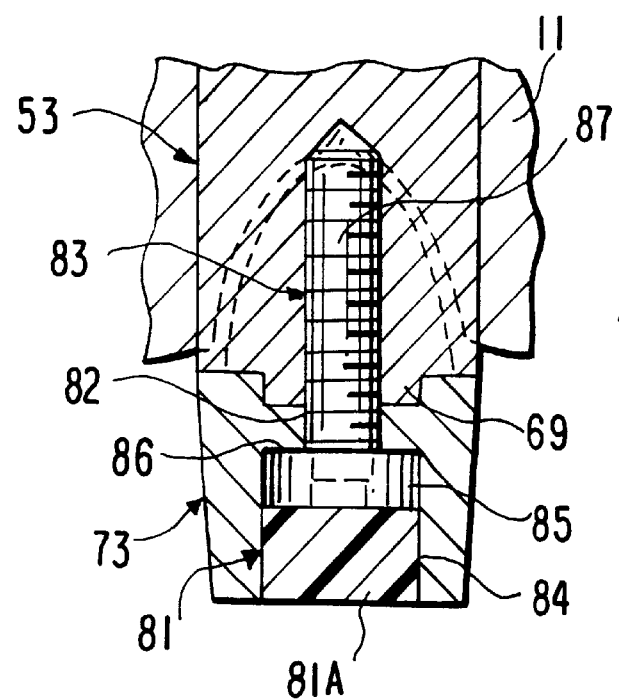
FIG. 13 is a partial front or facial cross-sectional view showing the attachment of the implant abutment to the implant body via the implant abutment screw and the insertion of a plug into the opening of the implant abutment of the inventive implant system.

Continuing with FIG. 3, implant abutment 73 of implant assembly 51 is made from a polished or machined smooth metal material such as a titanium alloy and is non-bone integrating. Abutment 73 has a cup-shaped configuration formed with an internal surface aspect 75 designed for selective mating engagement with coronal portion 63 of implant body 53 along non-bone integrating beveled surfaces 65. Implant abutment 73 also includes an external surface aspect 77 which leads to a coronal end 79 formed with an abutment opening 81 for receiving an abutment screw 83 comprising a circular head 85 and a cylindrical body 87, as described in greater detail hereinbelow. As best shown in FIG. 13, opening 81 includes a first wider passage 84 that leads into a second, narrower passage 82 and which together define an annular seating surface 86 on which head 85 of screw 83 is designed to rest.

Figure 14:
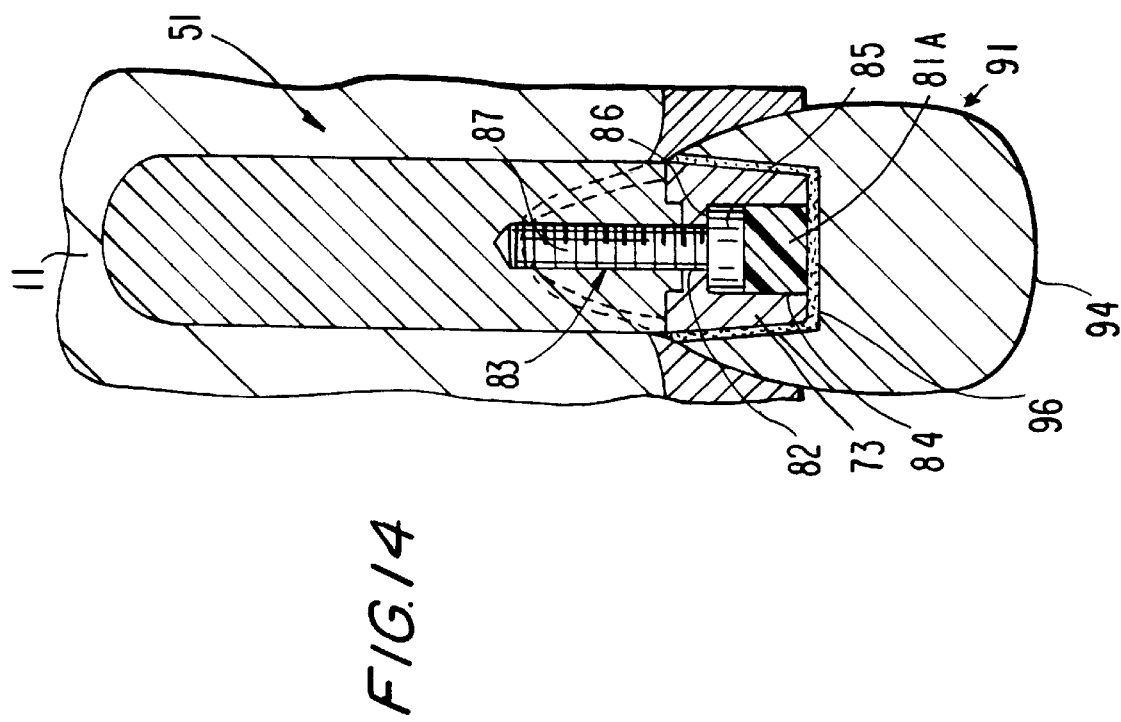
FIG. 14 is a front or facial cross-sectional view showing attachment of the crown to the implant abutment and attachment of the implant abutment to the implant body via the implant abutment screw of the inventive implant system.

Crown 91, as shown in FIGS. 3 and 14, has a cup-shaped configuration with an internal surface aspect 95 designed for mating engagement with external aspect 77 of implant abutment 73. Crown 91 is made from conventional dental metals and porcelain and also includes an external aspect 93 which leads to an incisal edge 94. Crowns 91, as shown in FIG. 16, have an interproximal contact point 94' where adjacent teeth touch and which serves to help form the base of papilla.

Figure 7:
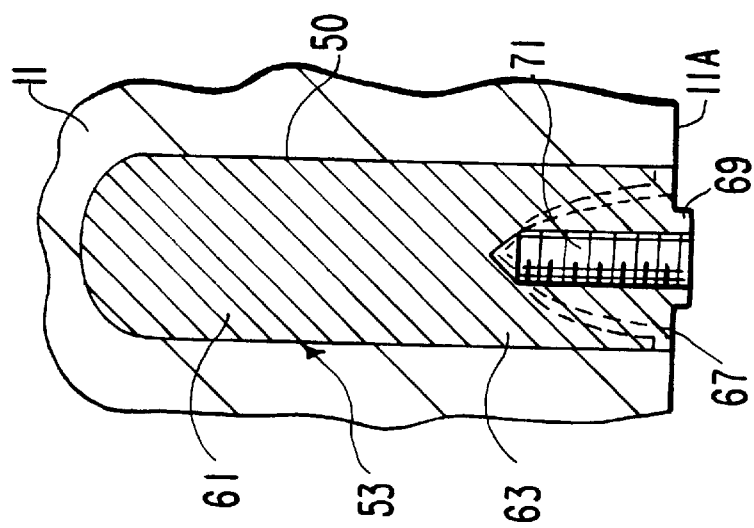
FIG. 7 is a front or facial cross-sectional view showing the step of insertion of the implant body of the inventive implant system into where the tooth root was previously located in the bone.

Referring now to FIGS. 7 and 14, as well as to FIG. 3, it is shown how implant assembly 51 of the invention is permanently affixed to bone 11 inside the mouth. The implant can be placed at the time of tooth extraction or in a previously edentulous site, provided adequate bone is present or can be grafted to the site, as is well known. After removal of the tooth root, and allowing for appropriate healing as well as conducting any necessary preparatory work in order to form an implant placement site 50 within bone 11, implant body 53 is fitted inside site 50 with plate 67 of coronal portion 63 extending flush with interproximal crestal bone 11A of bone 11 (see FIG. 7). To protect hex nut 69 and internal threads 70, a cover screw (not shown) is secured to hex nut 69 while implant body 53 is submerged inside bone 11. Healing time is approximately 3–6 months, during which implant body 53 is integrating to bone 11.

Figure 8:
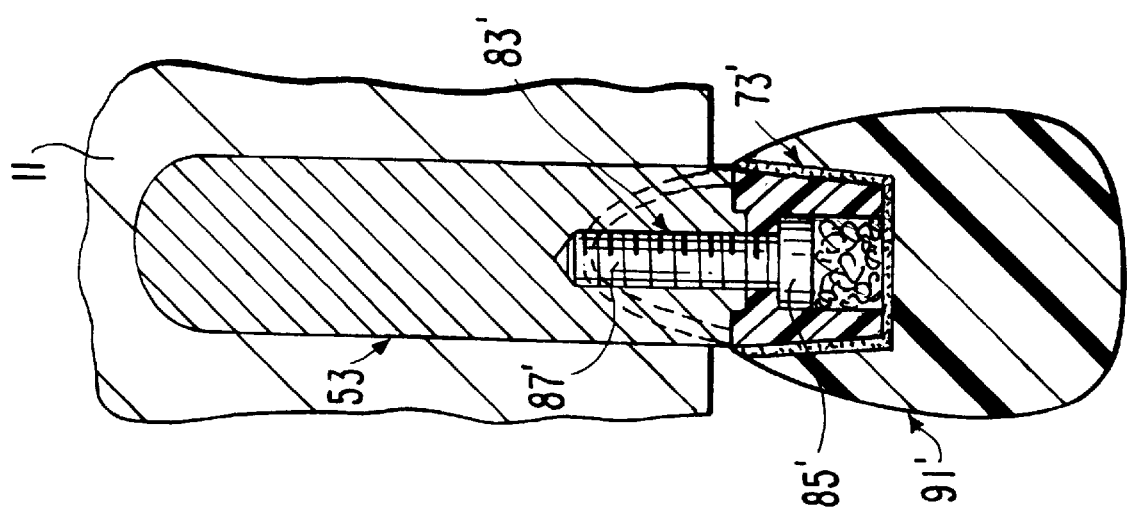
FIG. 8 is a front or facial cross-sectional view showing attachment of the implant healing abutment and temporary crown to the implant body of the inventive implant system.

Now referring to FIGS. 3, 4 and 8, after healing has been completed, an incision is made in the gingiva directly over hex plate 69. The protective cover screw (discussed above) is then removed. Any excess gingival tissue on facial aspect 55 or lingual aspect 57 along non-bone integrating beveled surface 65 of implant body 53 is also removed. As seen in FIG. 8, a temporary or healing abutment 73' made of a plastic material is secured to non-bone integrating beveled surface 65 of coronal portion 63 of implant body 53 by means of a screw 83' comprising a head 85' and a body 87'. This allows for proper soft tissue healing and as a means of initiating final soft tissue contours.

Temporary or healing abutment 73' may also retain a temporary crown 91' made of a plastic material in order to form and maintain papilla in a fashion similar to the final prosthesis. After soft tissue healing is completed, fabrication of the final implant supported crown or bridge prosthesis can be initiated. This is done with the use of implant impression copings and implant body analogues which are unique to the inventive system due to their shapes. An impression coping transfers the relationship of the implant and surrounding soft tissue in the mouth to the lab. The implant body analogue simulates the actual implant in the laboratory setting.

Figure 9:
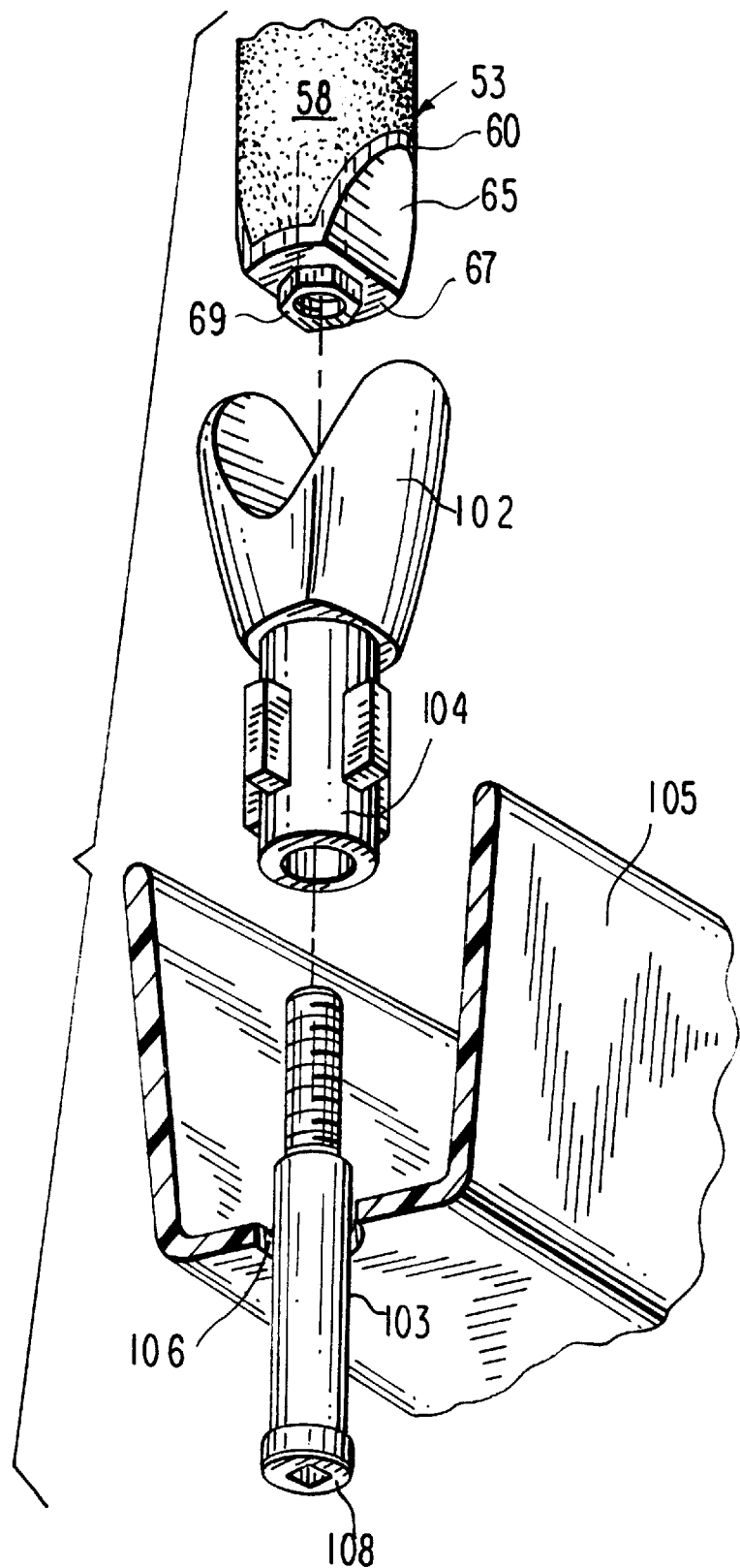
FIG. 9 is an exploded perspective view of the implant impression coping of the inventive implant system.
Figure 10:
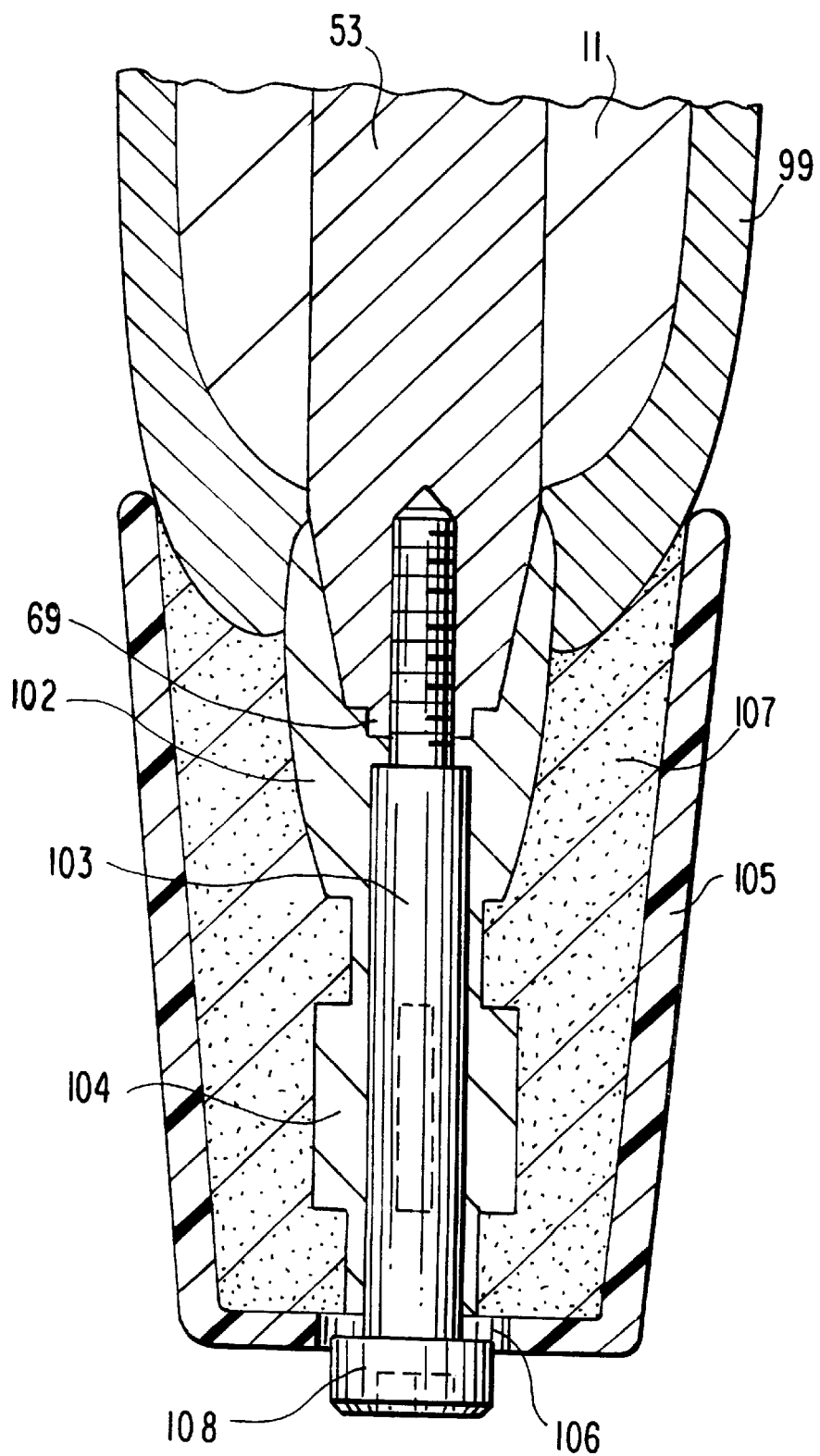
FIG. 10 is a cross-sectional view showing the implant impression coping in an assembled condition and attached to the implant body in the mouth.

Referring to FIGS. 9 and 10, an exploded view of implant impression coping 102 is seen. Impression coping 102 has a shaft 104 extending therefrom and is secured to coronal plate 67 and non-bone integrating beveled surface 65 of coronal aspect 63 of implant body 53 by means of screw 103. Screw 103 passes through shaft 104 for engagement to hex nut 69.

A conventional dental impression tray 105 with a hole 106, made over the area of the impression coping screw 103 to allow access to it, is filled with a conventional dental impression material 107 such as a polyvinyl siloxane substance. Impression tray 105 is seated in the mouth with head 108 of impression coping screw 103 accessible through tray hole 106. The entire assembly, as shown in FIG. 10, is allowed to set for approximately 6 minutes to allow for hardening of impression material 107. Once set, implant impression coping screw 103 is loosened and impression tray 105 is removed from the mouth with implant impression coping 102 embedded in impression material 107, which is held in impression tray 105.

Figure 11:
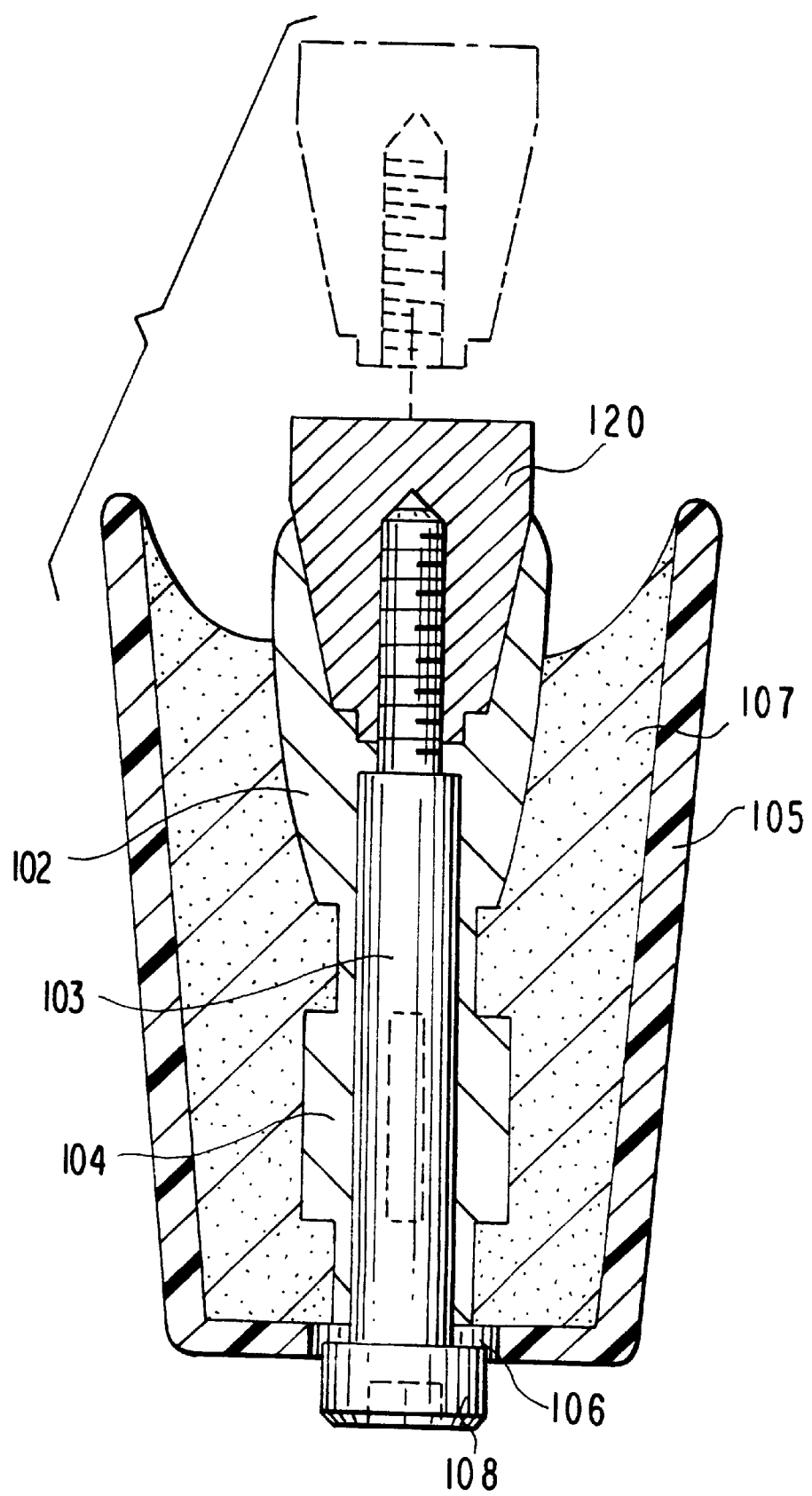
FIG. 11 is a cross-sectional view showing the implant body analogue secured to the implant impression coping.
Figure 12:
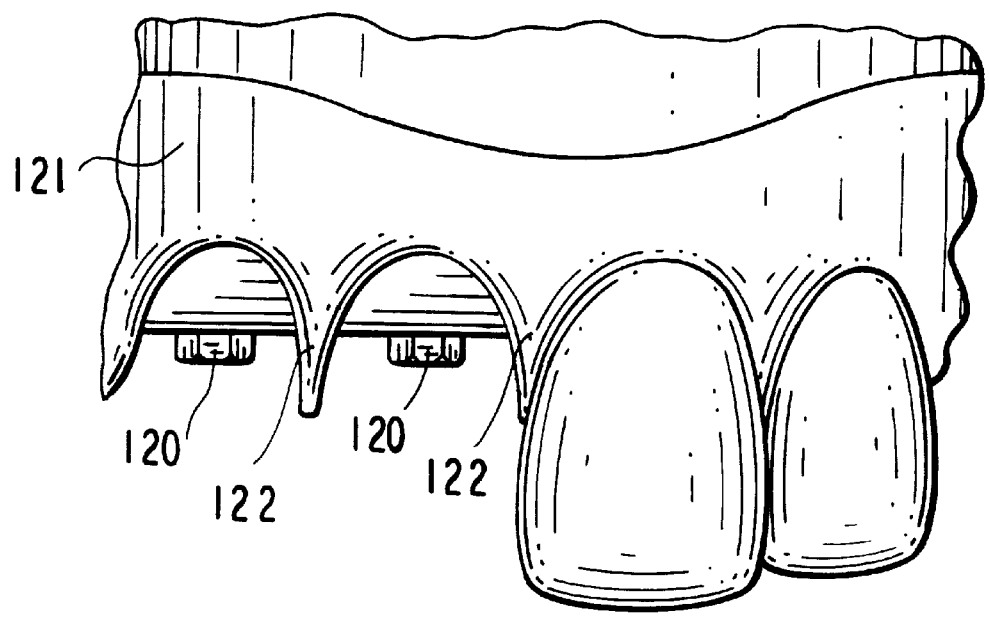
FIG. 12 is a front elevational or facial view showing the laboratory stone model with the implant body analogue in place.

Referring now to FIGS. 11 and 12, an implant body analogue 120 is attached to implant impression coping 102 via implant impression coping screw 103. This assembly is then poured in conventional dental stone to create a working dental laboratory model 121. Laboratory model 121, as seen in FIG. 12, with implant analogue 120 in place, reproduces the position of the implants in the mouth. It also serves to reproduce the soft tissue gingival contours including papillas 122 around the implants as well as adjacent tooth contours. This model 121 is used to assemble implant abutments 73 and to create the final implant supported dental crown or bridge prosthesis.

Referring now to FIGS. 3, 6, 13 and 14, implant abutment 73 is now coupled to coronal portion 63 of implant body 53 such that internal aspect 75 matingly engages coronal portion 63 along beveled surfaces 65 with abutment opening 81 aligned with screw hole 71 formed within coronal portion 63 of implant body 53. The underside of screw hole 81 of implant abutment 73 has the female equivalent (not shown) of external hex nut 69 for selective engagement therewith. Then, abutment screw 83 is used to secure implant abutment 73 to implant body 53. Abutment screw 83 includes head 85 formed with an outside operating slot 89 (see FIG. 3) and screw body 87 formed with a plurality of outer threads 88.

As shown in FIGS. 13 and 14, abutment screw 83 is first inserted into abutment opening 81 of abutment 73 through first passage 84 such that screw body 87 is enabled to be rotatably threaded through hex nut 69 and into screw hole 71. When properly engaged, head 85 of abutment screw 83 abuts against surface 86 defined by first and second passages 84 and 82 formed by abutment opening 81. The space remaining over screw head 85 and abutment opening 81 is filled with a plug 81A made of a plastic rod material of the same dimension as abutment opening 81 and is cut in length to fit this space. The purpose of plug 81A is to prevent microvibration of implant abutment 73 during function from loosening screw 83 and thereby prevent it from backing out of abutment opening 81.

As shown in FIG. 14, as well as FIGS. 16–17, crown 91 is then coupled over implant abutment 73. In particular, internal aspect 95 of crown 91 is engaged to external aspect 77 of implant abutment 73 by means of a conventional dental cement 96.

Figure 15:
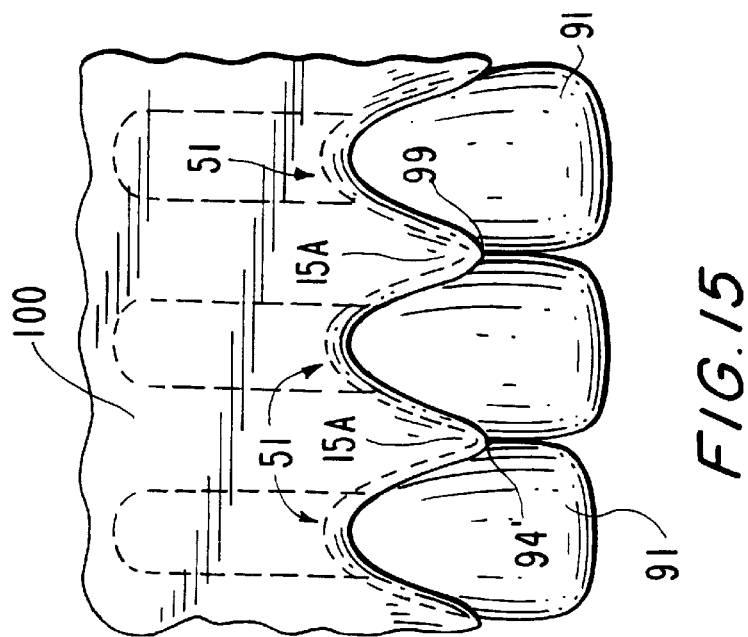
FIG. 15 is a front elevational or facial view showing side-by-side implants of the inventive implant system with final prosthesis in place and disposed in a patient's mouth.

In accordance with the invention, several implant assemblies 51 may be used to replace side-by-side teeth, creating the configuration depicted in FIGS. 15 and 16. As can be appreciated, when the inventive implant design is used, the gingival or gum tissue 100 (see FIG. 15) assumes a scalloped appearance as it follows the shape of bone integrating external surface 58 of implant body 53 (see FIG. 14). Consequently, papilla 15A is formed between the side-by-side implant assemblies 51 of the invention and has an interproximal base 99 (corresponding to the contact point 94' between adjacent crowns 91) which measures a distance B not greater than 5 mm past interproximal crestal bone 11A of bone 11. This is in direct contrast to all other prior art techniques, which fail to enable papilla to form naturally between adjacent implants producing aesthetically unacceptable black spaces where the papilla is normally located.

Referring now to FIGS. 5 and 17, it can be appreciated that each beveled surface 65 defines a taper C (FIG. 5) when viewed along interproximal aspect 59 which, in accordance with the invention, extends inwardly towards underlying plate 67 in an amount between about 5 and 25 degrees. It is important to have this taper in order to create an appropriate path of insertion for the securement or attachment of the implant abutment to the implant body as well as to allow for the attachment and securement of the crown or prosthesis to the implant abutment and to allow for proper crown/prosthetic contours.

A significant feature of the inventive design is the inclusion of a non-bone integrating beveled surface along the facial aspect of the coronal portion of the implant body for maintaining bone around the implant body at two different levels in side-by-side implants and/or adjacent natural teeth, thereby allowing gingival tissue to be maintained also at two different levels so that a scalloped natural looking appearance of the gingival tissue including papilla is produced.

It will thus be seen that the objects set forth above, among those made apparent from the proceeding description, are efficiently attained and, since certain changes may be made in the above construction without departing from the spirit and scope of the invention, it is intended that all matter contained in the description and shown in the drawings shall be interpreted as illustrative, and not in a limiting sense.

It is also to be understood that the claims are intended to cover all of the generic and specific features of the invention, and all statements of the scope of the invention, which, as a matter of course, fall therebetween.

What is claimed is:

1. A dental implant system comprising:
    an implant body having a facial surface aspect, lingual surface aspect and interproximal surface aspect and which is defined by an apical portion and a coronal portion;
    an implant abutment having an internal surface aspect for selective mating engagement with the coronal portion of said implant body and also having an external surface aspect;
    a crown having an internal surface aspect for selective mating engagement with the external aspect of said implant abutment;
    wherein said implant body has a bone integrating external surface which in a coronal direction extends more along said interproximal aspect than along said facial aspect, and wherein said bone integrating surface defines a non-bone integrating beveled surface along the facial aspect of the coronal portion of said implant body.

2. The system of claim 1, wherein said bone integrating surface further defines a non-bone integrating beveled surface along the lingual aspect of the coronal portion of said implant body.

3. The system of claim 1, wherein said beveled surface comprises a facial scallop having an apical extent and a coronal extent.

4. The system of claim 3, wherein said beveled surface defines a taper viewed along said interproximal aspect which extends inwardly from said apical extent to said coronal extent at an angle of an amount between about 5 degrees and 25 degrees.

5. The system of claim 3, wherein between said bone integrating surface and said non-bone integrating beveled surface is a non-bone integrating scalloped shaped collar.

6. The system of claim 3, wherein said beveled surface has a distance between said apical extent and said coronal extent in an amount between about 2 and 6 mm.

7. The system of claim 1, wherein said internal aspect of said abutment is selectively engaged to said coronal portion of said implant body by means of a screw.

8. The system of claim 7, wherein said screw is maintained in position for engaging said internal aspect of said abutment to said coronal portion of said implant body by means of an overlying plug.

9. A dental implant body comprising an apical portion and a coronal portion and having a facial surface aspect, lingual surface aspect and interproximal surface aspect, and further having a bone integrating external surface which in a coronal direction extends more along said interproximal aspect than along said facial aspect, and wherein said bone integrating surface defines a non-bone integrating beveled surface along the facial aspect of the coronal portion of said implant body.

10. The body of claim 9, wherein said bone integrating surface further defines a non-bone integrating beveled surface along the lingual aspect of the coronal portion of said implant body.

11. The body of claim 9, wherein said beveled surface comprises a facial scallop having an apical extent and a coronal extent.

12. The body of claim 11, wherein between said bone integrating surface and said non-bone integrating beveled surface is a non-bone integrating scalloped collar.

13. The body of claim 11, wherein said beveled surface defines a taper viewed along said interproximal aspect which extends inwardly from said apical extent to said coronal extent at an angle of an amount between about 5 degrees and 25 degrees.

14. The body of claim 11, wherein said beveled surface has a distance between said apical extent and said coronal extent in an amount between about 2 and 6 mm.

* * * * *